United States Patent [19]

DeVaughn

[11] Patent Number: 5,260,030
[45] Date of Patent: Nov. 9, 1993

[54] CALIBRATED PIPETTE TIP AND METHOD

[75] Inventor: Donald H. DeVaughn, San Francisco, Calif.

[73] Assignee: Bio-Plas, Inc., San Francisco, Calif.

[21] Appl. No.: 893,250

[22] Filed: Jun. 3, 1992

[51] Int. Cl.⁵ .............................................. B01L 3/02
[52] U.S. Cl. ................................. 422/100; 73/864.01; 73/864.11; 73/864.74; 422/102
[58] Field of Search .......................... 422/100, 102; 73/864.11, 864.01, 864.74

[56] References Cited

U.S. PATENT DOCUMENTS

| | | | |
|---|---|---|---|
| 3,938,392 | 2/1976 | Rodrigues | 73/864.11 |
| 4,124,044 | 11/1978 | Nugent | 141/98 |
| 4,237,095 | 12/1980 | Suovaniemi et al. | 422/100 |
| 4,256,120 | 3/1981 | Finley | 422/100 |
| 4,275,591 | 6/1981 | Wand | 73/864.01 |
| 4,335,718 | 6/1982 | Calabrese | 604/272 |
| 4,461,185 | 7/1984 | Schoffel | 73/864.74 |
| 4,679,446 | 7/1987 | Sheehan et al. | 73/863.13 |
| 4,909,991 | 3/1990 | Oshikubo | 422/100 |
| 4,979,402 | 12/1990 | Ryan et al. | 422/102 |

FOREIGN PATENT DOCUMENTS 3701250 1/1987 Fed. Rep. of Germany .
1206336 8/1958 France .
276042 4/1988 Japan .
2090164 12/1981 United Kingdom .

*Primary Examiner*—Jill A. Johnston
*Assistant Examiner*—Ramon Torres
*Attorney, Agent, or Firm*—Flehr, Hohbach, Test, Albritton & Herbert

[57] ABSTRACT

A pipette tip (30) for use with a pipetter (10) and a method for dispensing a precise volume of a fluid (54). The pipette tip (30) has a hollow body (32), which defines an interior volume (34), and a channel (42) therein having a calibrated volume. Channel (42) extends from an intake opening (44) to an overflow opening (46) positioned inside the interior volume (34) of the tip above a reservoir portion (50) inside the tip. Fluid (54) drawn through the intake opening (44) and into the channel (42) in excess of the calibrated channel volume is gravity-shed or sloughed into an overflow reservoir (50). Thus, a calibrated volume of fluid (54) remains in the channel (42) and can be dispensed accurately from the channel (42). Additionally, the reservoir portion (50) captures and contains the overflow fluid in a stable condition, permitting the reservoir (50) to be used to react various substances (76, 77) with the overflow fluid (56a) inside the pipette tip (30). The internal reservoir (50) also may be divided by a partition (72) to provide a plurality of reservoirs or sub-volumes (73, 74) inside the pipette tip (30).

24 Claims, 4 Drawing Sheets

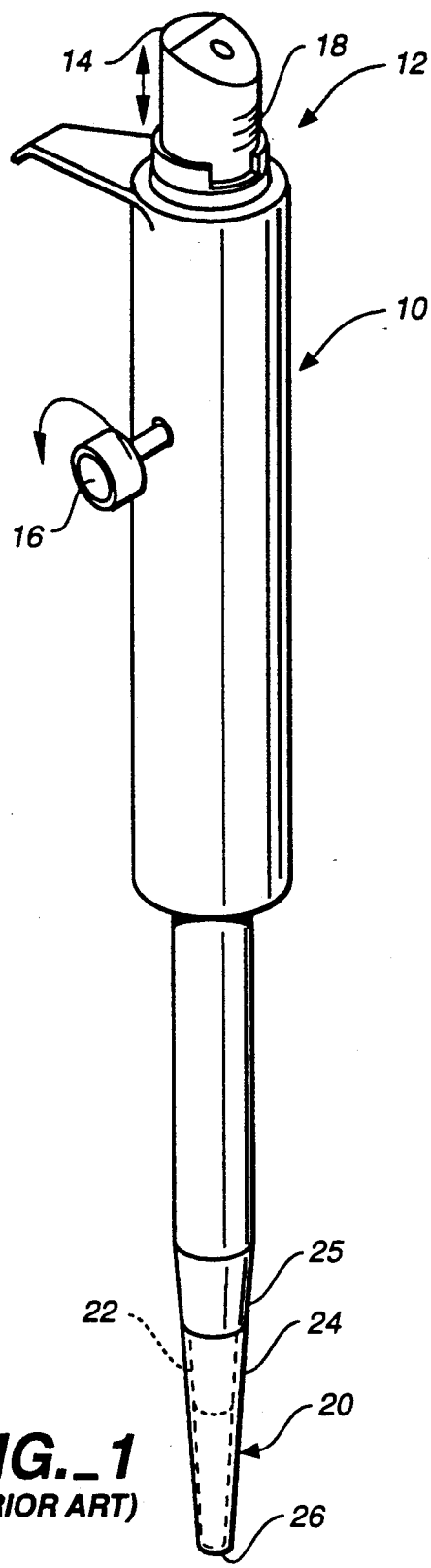
FIG._1
(PRIOR ART)
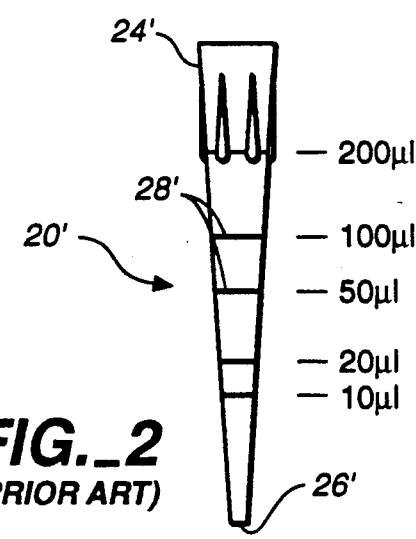
FIG._2
(PRIOR ART)

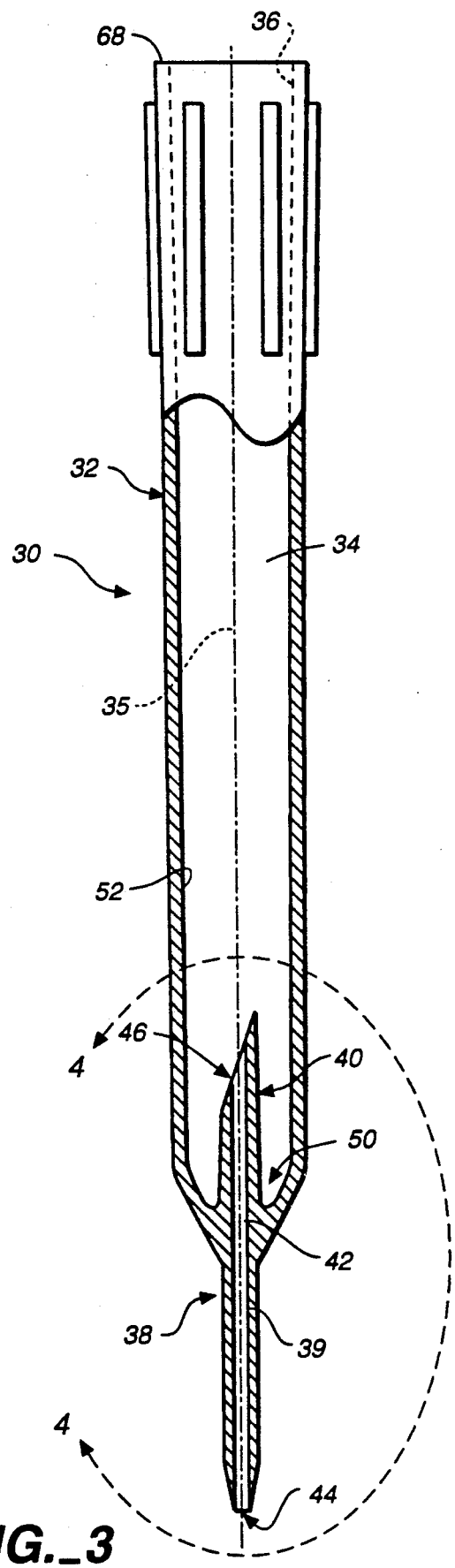
FIG._3
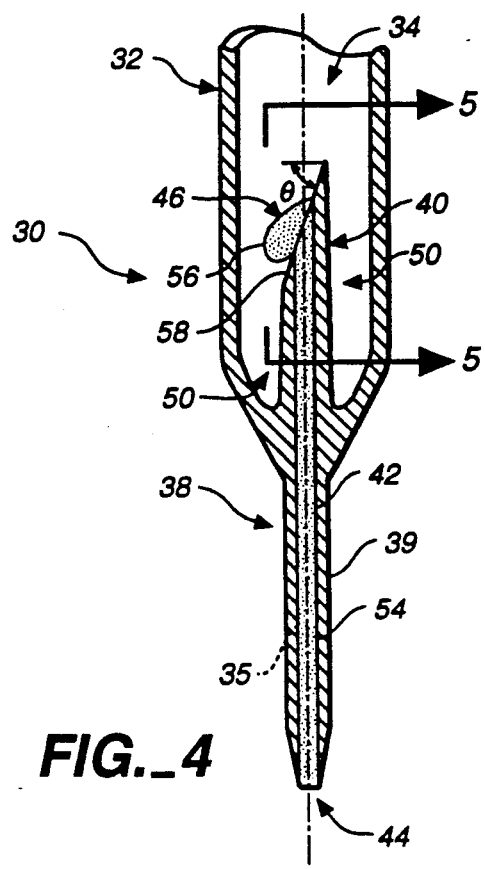
FIG._4
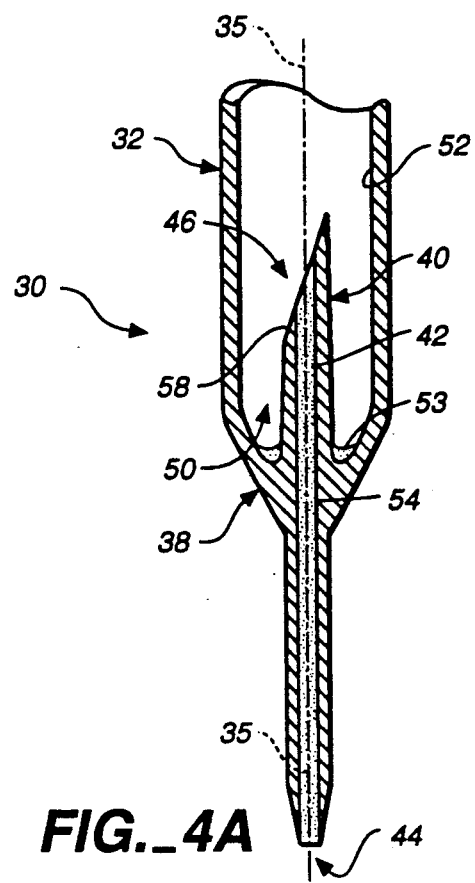
FIG._4A

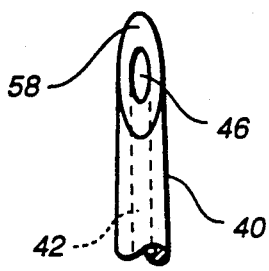
FIG._5
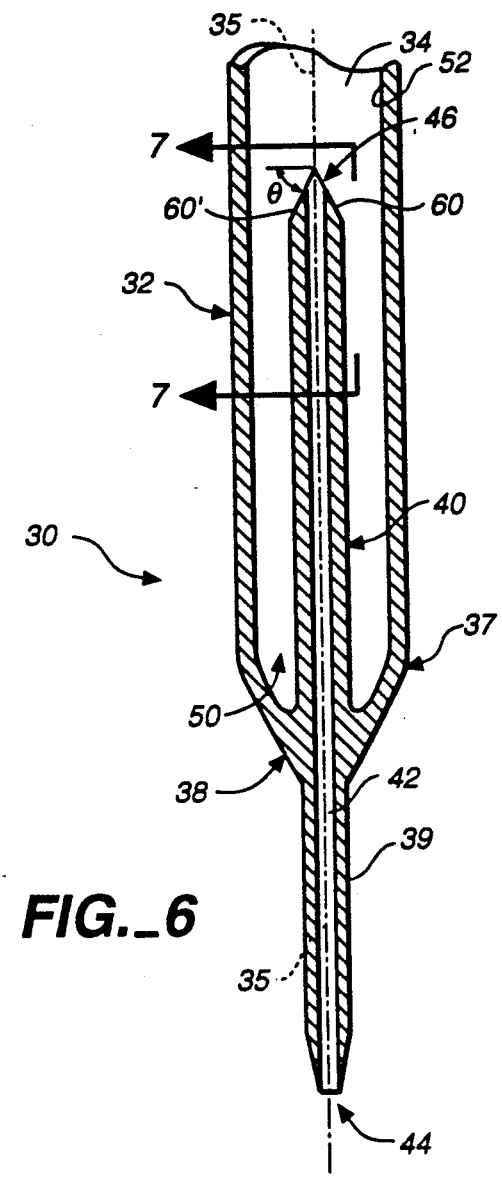
FIG._6
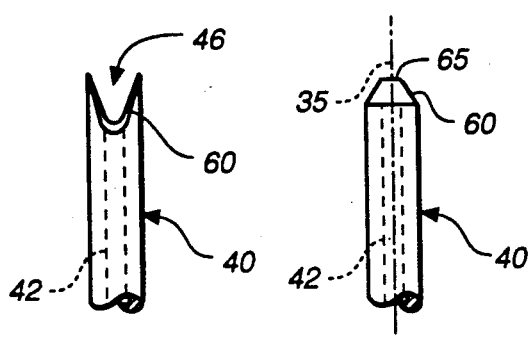
FIG._7
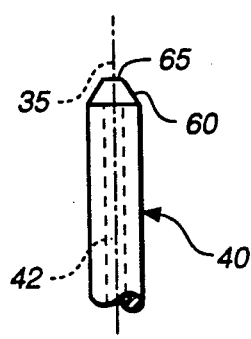
FIG._7A
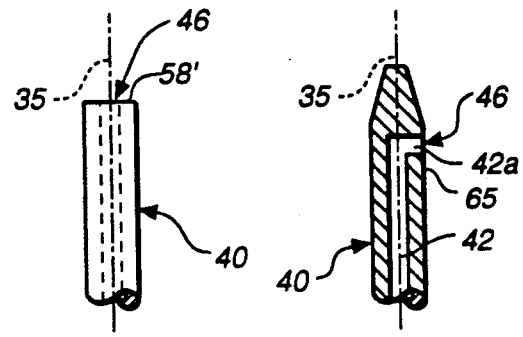
FIG._7B
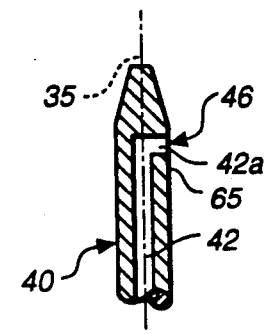
FIG._7C

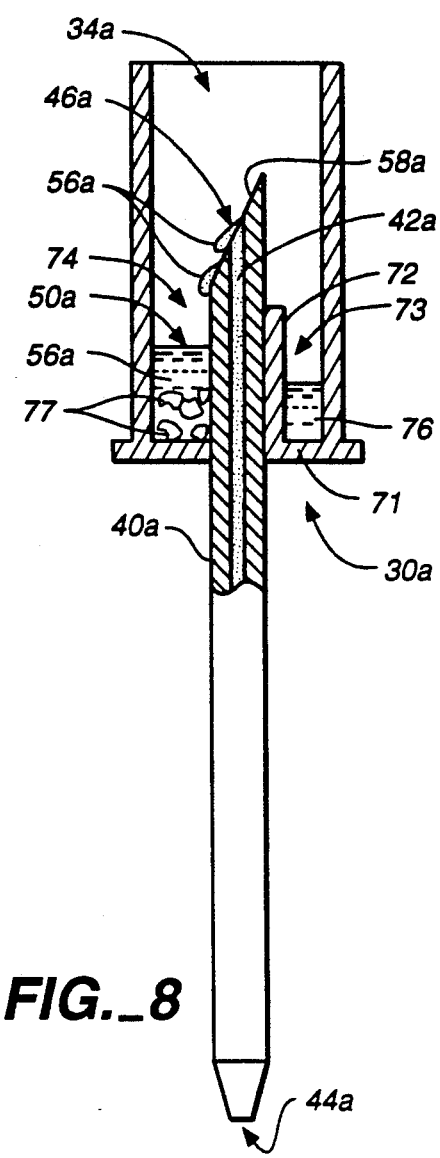
FIG._8
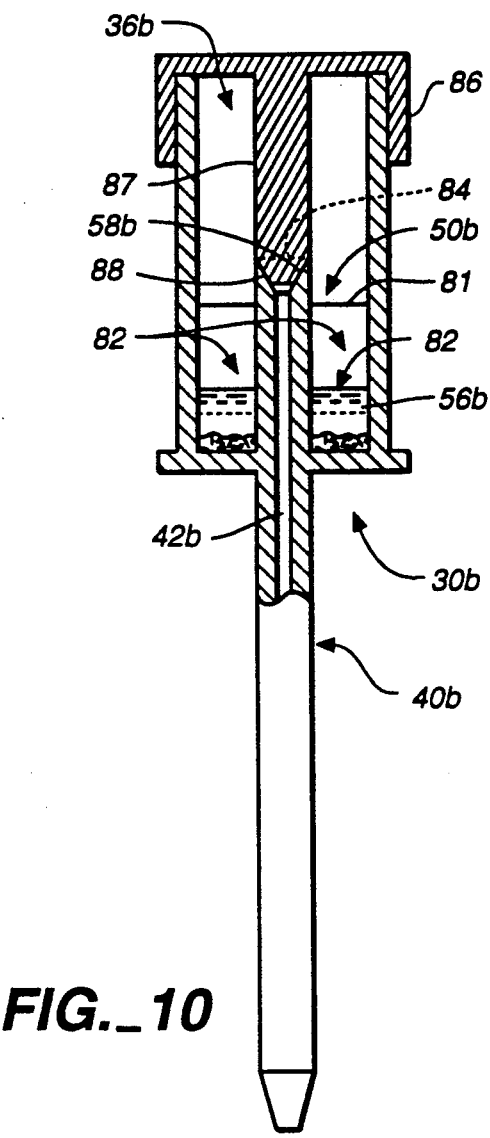
FIG._10
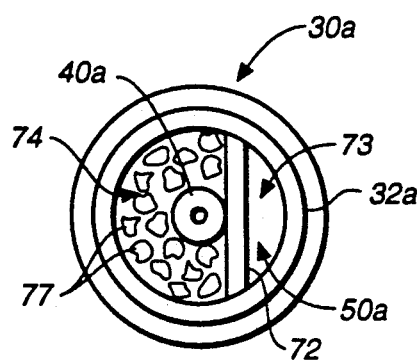
FIG._9
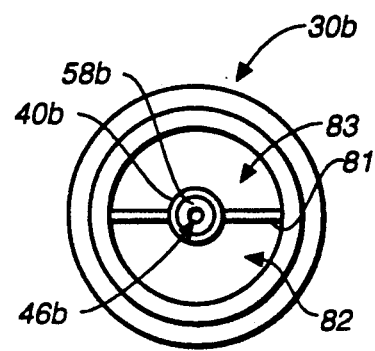
FIG._11

CALIBRATED PIPETTE TIP AND METHOD

TECHNICAL FIELD

The present invention relates, in general, to pipette assemblies and methods for pipetting liquids and, more particularly, relates to the pipette tip component of pipette assemblies and to methods used to dispense a calibrated volume of liquid using a pipette assembly.

BACKGROUND ART

As the biotechnology, pharmaceutical and chemical industries grow, their laboratory research and development proportionately expands. Thus, research precision has become increasingly important, often distinguishing the efforts of one company or group from another. Thus, research apparatus and techniques, once thought to represent the industry standard, are continually being replaced by better, more efficient and more accurate apparatus and techniques.

In particular, the use of pipetting assemblies has rapidly increased in volume and simultaneously has increasingly required more accuracy, as minute differences often dictate success or failure. Pipette assemblies have traditionally included two basic components, namely, the pipetter and the hollow pipette tip. The pipetter is a device for creating a pressure differential inside the pipette tip. When a negative pressure or vacuum is present in the tip, liquid is drawn into the tip. When a positive pressure is created, or the vacuum is released, the liquid is forced from or gravitates from the tip.

Early pipette assemblies employed relatively simple pipetters and pipette tips which included volumetric marks or lines. The technician would merely draw fluid into the tip until it reached the reference line. The accuracy of this approach depended upon the technician's skill and the accuracy of calibration of the reference marks, neither one of which could be safely relied upon when a high degree of precision was required.

Subsequently, considerable effort has been directed toward providing adjustable mechanical and electromechanical pipetters which can be adjusted to a volume and then have that volume calibrated. Pipetter devices can be divided into two broad categories, namely, the "to-deliver" and the "to-contain" pipetters. A "to-deliver" pipetter overdraws the amount of fluid desired, but delivers, dispenses or discharges an only pre-determined or adjusted volume, which can be accurately calibrated. "To-contain" pipetters draw an adjusted volume of liquid and then dispense or discharge that entire volume. Regardless of the type of mechanical pipetter, they typically employ a piston and cylinder arrangement which, through air displacement, draws the desired fluid into the disposable pipette tip and delivers or dispenses the liquid from the tip at a later time.

FIG. 1 illustrates a typical mechanically adjustable pipetter device 10 which includes a piston and cylinder assembly (not shown). The piston and cylinder are generally of a known diameter and the stroke of the piston is coupled to a volume adjustment mechanism 16 having a vernier scale or indicator 12 shown proximate the upper end of pipetter 10. In pipette assembly 10, volume adjustment mechanism 16 also includes a displaceable button 14. Volume indicia 18 at indicator 12 allows the technician to set the proposed volume of fluid to be drawn or dispensed. By accounting for the differences in the specific gravities between the air and the desired fluid, as well as the viscosity difference, the drawn volume of liquid can be reasonably accurately set. Once the desired volume is set, button 14 may be depressed to displace air from the cylinder. Upon the return stroke of the piston, a corresponding volume of fluid is drawn into a reservoir or pipette tip 20.

Typical of adjustable pipetters are the pipetters sold under the trademarks EPPENDORF®, PIPETMAN®, FINNPIPETTE, EXCALIBUR®, SOCOREX and OXFORD®, to name a few. One problem which exists with these adjustable pipetters is that the volume indicated on the volume adjustment mechanism often is not an accurate determination of the actual amount of fluid withdrawn or dispensed. The pipette volume, generally, needs to be calibrated every time the volume is adjusted or set. Furthermore, even once fixed and calibrated, the volume should be recalibrated every week, although this is rare in actual practice. Thus, even adjustable pipetters having supposedly known or calibrated dispensing volumes will dispense volumes of liquid which vary from the nominal pre-set or adjusted volume.

Another problem associated with calibrated mechanical pipetters 10 is that various environmental factors, such as room temperature and atmospheric pressure, influence the accuracy of the fluid volume drawn or dispensed. Additionally, pipetter 10 often will be cradled in the research technician's hand, which may raise the temperature of the piston/cylinder arrangement so that thermal expansion causes inaccurate draws or deliveries.

A further problem experienced by adjustable mechanical pipetters is that the internal mechanisms can wear or fatigue. Excessive use may deteriorate the mechanical parts, for example, the spring used to urge the piston upward during the fluid draw. A worn or fatigued spring may not urge the piston to its full draw or may lead to inconsistencies on successive draws. Moreover, the O-ring assemblies may crack or leak causing the piston/cylinder arrangement to lose pressure. These above-mentioned mechanical breakdowns, in addition to the research technician's level of competence and/or fatigue, vary the fluid volume draws or deliveries, even with a "calibrated" adjustable mechanical pipetter.

Briefly, pipette tips 20 are usually provided by disposable plastic tips which are slidably and frictionally held on a tip mounting portion 22 located at the bottom end of pipetter 10. Pipette tips 20 may be hollow cylindrical or conical members which extend from a pipetter mounting end 24 to a liquid intake end 26.

In an attempt to alleviate some of the problems encountered in connection with adjustable pipetters, disposable pipette tips 20 having visual indicators or markings for estimating the amount of the drawn or dispensed fluids have been used with mechanical pipetters. As shown in FIG. 2, a disposable pipette tip 20' of the prior art is illustrated which can be slidably mounted to tip mounting portion 22 of pipetter assembly 10, shown in FIG. 1. This pipette tip is commercially available under the trademark REFERENCE TIP®, and it has volume reference marks visually perceptible on the exterior of the tip. Thus, pipette tip 20' includes visual indicia 28' up to 200 µL. Accordingly, the research technician can use these indicia to visually confirm the accuracy of the draw of volume adjustable pipetter 10. The volumes indicated by the reference marks 28' are only approximate volumes, and when such pipette tips are used with adjustable mechanical pipetters, these markings are intended to act only as a confirmation of the volume drawn by the mechanical pipetter.

There are numerous patents directed to pipetters, but relatively few relating to the pipette tips. In U.S. Pat. No. 4,909,991 to Oshikubo, for example, a pipetter is disclosed which is constructed in a manner that attempts to minimize the volumetric change which can occur as a result of the elevated temperature of the user's hand. In U.S. Pat. No. 4,679,446 to Sheehan et al., a pipetter is disclosed in which there are several chambers or volumes of differing size in the pipetter which can be used to draw liquid. A set of pipette tips of differing size is provided which cooperates with the pipetter to determine which fluid intake channels or pathways to the various chambers are open to draw fluid.

U.S. Pat. No. 4,237,095 to Suovaniemi is directed to a disposable pipette tip construction which is designed to produce air bubbles that do no adhere to the walls of the pipette tip during dispensing of multiple doses or volumes. Thus, when a small volume is dispensed and the pipetter piston returned to its normal position for dispensing the next volume, air bubbles are drawn into the tip and rise to the top of the liquid column remaining in the tip. The tip construction of this patent causes the air bubbles to rise in the center of the liquid column, rather than become adhered to one side or the other of the pipette tip.

Finally, U.S. Pat. Nos. 4,275,591 to Wand and 4,124,044 to Nugent both disclose protective shield assemblies which have been used with pipette tips.

As will be apparent, however, none of this patent art discloses a pipette tip construction which itself is capable of producing a draw and/or delivery of a calibrated or calibratable volume of liquid. All of these prior art references depend upon the pipetter mechanism's ability to control the drawn or delivered volume.

Traditionally, pipette assemblies have been widely used in connection with chemical and biochemical reactions. Thus, the pipette assembly is used to draw a liquid and thereafter deliver or dispense it to a container or vessel for its use in a chemical or biochemical procedure. The liquid may be reacted in the vessel with a reagent or it may be stored to permit reactions to occur over time or in response to variations in the ambient storage parameters.

This sequence of drawing and dispensing to a separate container requires in both the container and the pipette tip are contacted with the liquid, and that a liquid transfer also takes place. In some procedures, the liquid may contaminate both the pipette tip and the container as soon as it contacts the same. For other procedures, the liquid can be dangerous, making transfer to the container a safety hazard.

Existing pipette tips, however, have not been constructed in a manner allowing their use not only to draw liquid, but also as a reaction vessel in which the liquid can be stored and/or reacted with various reagents.

Accordingly, in one aspect of the present invention, it is an object to provide a pipette tip which is capable of accurately dispensing a calibrated liquid volume independently of the accuracy of the volume calibration of the pipetter.

It is another object of the present invention to provide a disposable pipette tip which facilitates pipetting accuracy.

Still another object of the present invention is to provide a pipette tip and method of pipetting which more accurately dispenses fluids despite inconsistencies in the pipetter or technician's technique.

In another aspect of the present invention, it is an object to provide a pipette tip and method which enable the pipette tip to be used not only to draw in liquids, but also to be used as a container for chemical and biochemical reactions.

It is a further object of the present invention to provide a pipette tip apparatus which is durable, compact, has a minimum number of components, is easy to use by unskilled personnel, and is economical to manufacture.

The apparatus of the present invention has other objects and features of advantage which will be more readily apparent from the following description of the Best Mode of Carrying Out the Invention and the appended claims, when taken in conjunction with the accompanying drawing.

DISCLOSURE OF INVENTION

The pipette tip of the present invention is intended for use with a device for producing a pressure differential in the pipette tip, such as a pipetter, in order to enable the drawing and dispensing of a calibrated volume of fluid. The present pipette tip comprises, briefly, a hollow body which defines an interior volume. The hollow body includes a channel or tube extending from an exterior intake opening to an overflow opening positioned inside the hollow body. In one aspect of the present invention, the channel or tube between the intake opening and the overflow openings have a precise fixed volume which can be accurately calibrated. The inner end of the channel or tube defining the overflow opening preferably is formed to cause liquid drawn into the channel in excess of the fixed or calibrated volume to be gravity-shed or sloughed into a reservoir portion of the interior volume of the pipette tip so that the fluid remaining in the channel or tube is very precisely and automatically drawn to a known amount. In another aspect of the invention, the channel extends into the interior volume of the pipette tip in a manner enabling the interior volume to act as a storage container and/or contain a reagent material and act as a reaction container.

The method of the present invention in the first aspect, therefore, is comprised, briefly, of the steps of drawing a fluid into a pipette tip through a fluid channel having a fixed volume until the fluid fills and overflows out of the channel through an overflow opening and into an interior volume of the pipette tip, and thereafter displacing the fluid remaining in the fluid channel from the pipette tip to dispense a fixed fluid volume which can be calibrated. The method of the present invention in its second aspect is comprised, briefly, of the steps of urging fluid into a hollow pipette tip having a reservoir portion in an interior volume thereof until the liquid overflows into such reservoir portion and then using said reservoir portion as a container for said fluid for storage and/or reaction with a reagent material placed in said reservoir portion.

BRIEF DESCRIPTION OF THE DRAWING

FIG. 1 is front perspective view of a typical prior art pipette assembly including a pipetter and pipette tip.

FIG. 2 is a front elevation view of a prior art disposable pipette tip with volume reference markings.

FIG. 3 is an enlarged, side elevation view, in partial cross section, of the pipette tip constructed in accordance with the present invention.

FIG. 4 is a further enlarged, side elevation view, in cross-section, of the area of the pipette tip of FIG. 3 bounded line 4—4.

FIG. 4A is an enlarged, side elevation view corresponding to FIG. 4 and showing an overdraw of liquid.

FIG. 5 is a fragmentary, side elevational view of an interior end of a calibrated tip channel and an overflow opening, taken substantially along the plane 5—5 of FIG. 4.

FIG. 6 is an enlarged, fragmentary, front elevation view, in cross-section, of an alternative embodiment of the pipette tip of the present invention showing an increased channel volume and an alternative overflow opening.

FIG. 7 is a fragmentary, side elevational view of the inner end of the fluid channel and the overflow opening, taken substantially along the plane 7—7 of FIG. 6.

FIG. 7A is a fragmentary, front elevation view of the inner end of an alternative embodiment of the fluid channel and overflow opening corresponding to FIG. 6.

FIG. 7B is a fragmentary, front elevation view of the inner end of a further alternative embodiment of the fluid channel and overflow opening corresponding to FIG. 6.

FIG. 7C is a fragmentary, front elevation view, in cross section of the inner end of another alternative embodiment of the fluid channel and overflow opening corresponding to FIG. 6.

FIG. 8 is an enlarged side elevation view of a further alternative embodiment of the pipette tip of the present invention.

FIG. 9 is a top plan view of the pipette tip of FIG. 8.

FIG. 10 is an enlarged side elevation view of still a further alternative embodiment of the pipette tip of the present invention, with an end closure cap mounted thereon.

FIG. 11 is a top plan view of the pipette tip of FIG. 10, with the cap removed.

THE BEST MODE OF CARRYING OUT THE INVENTION

The pipette tip of the present invention facilitates pipetting accuracy, even though there may be user or pipetter inconsistencies, and it affords the user new flexibility in performing chemical and biochemical procedures. While the present invention has been described with reference to a few specific embodiments, the description is intended to be only illustrative of the invention and is not to be construed as limiting the invention. Various modifications to the present invention can be made to the preferred embodiments by those skilled in the art without departing from the true spirit and scope of the invention, as defined by the appended claims.

Referring now to FIGS. 3 and 4, a pipette tip, generally designated 30, is illustrated, which may be employed with a pipetter, such as pipetter 10 of FIG. 1, to accurately and reproducibly dispense a fixed volume of fluid which can be calibrated. Pipette tip 30 is formed with a hollow body 32 which defines an interior volume 34. In accordance with the present invention, pipette tip body 32 is further formed with a fluid channel means 42 extending from an inlet orifice or intake opening 44 to an overflow orifice or opening 46. Overflow opening 46 is positioned for the overflow of fluid from channel means 42 into interior volume 34 of the pipette tip, preferably in a direction away from opening 46. Most preferably, such overflow of fluid is gravity-induced to flow away from overflow opening 46, which is positioned above a reservoir portion 50 of interior volume 34 of the pipette tip.

In order to enable dispensing of a predetermined or known volume of fluid, channel means 42 is formed to have a fixed volume between intake opening 44 and overflow opening 46 which can be accurately calibrated. Thus, channel means 42 may advantageously take the form of an elongate hollow fluid receptacle having a fixed or calibrated volume. As used herein, therefore, the expressions such as "calibrated channel", "calibrated volume" and "channel means having a calibrated volume" shall mean a channel, receptacle or bore having a fixed volume which can be a calibrated, or a determined, or a known volume. Thus, once channel means or receptacle 42 is filled completely, a corresponding calibrated volume of fluid or liquid will be present in channel 42. It is not necessary to overflow channel means 42, but further over-drawing or intake of liquid into elongate receptacle or channel means 42 merely overflows such additional fluid into a second receptacle or internal reservoir portion 50 of interior volume 34, as best may be seen in FIG. 4A, without increasing the volume of liquid remaining in channel means 42.

Pipette tip 30 further includes mounting means, such as a mounting opening 36, for mounting of the tip on a device, such as pipetter 10, for urging fluid into interior volume 34 through channel means 42.

Hollow pipette tip body 32 is preferably an elongated, cylindrical or conical, tubular structure having a longitudinal axis 35. Even generally cylindrical tubular bodies 32, however, may taper slightly inwardly from the pipette mounting end 36 to proximate fluid intake end 38, for example, to accommodate removal of molding core pins. Fluid intake end 38 preferably includes a downwardly extending tubular section 39 which defines a portion of calibrated channel means 42 and terminates fluid intake opening 44.

Preferably, calibrated channel means 42 is provided by a single channel or bore, but it will be understood that a plurality of calibrated bores could be employed. A pipette tip constructed in accordance with the present invention, for example, might include two channel means of fixed volumes. The volumes could be the same or different, and the intake and overflow openings could be located at the same or differing axial positions along axis 35. Side-by-side channels might be sufficiently laterally spaced to enable drawing of liquid from side-by-side sources.

Channel means 42 preferably is integrally formed with fluid intake end 38 of body 32. Thus, tubular wall portion 40 protrudes into interior volume 34 and defines, with body 32 reservoir portion 50, while integral tubular end 38 protrudes outwardly. Channel or bore 42 extends over the length of these two tubular body portions. This construction enables the tip to be injection-molded-, for example, from polyethylene and a channel-forming core can be pulled downwardly to form channel 42.

In an alternative embodiment of the pipette tip of the present invention shown in FIGS. 8 and 9, a tubular channel means is formed independently of the tip body, with the tubular channel being inserted through and secured to an opening in a bottom end of the body. It will be noted that a hermetic seal exists between the tubular channel member and body, for example, as the result of using a sealing adhesive, in order for this form of tip to maintain a negative pressure for drawing in fluid.

During the manufacture of pipette tip 30, the volume or fluid capacity of channel 42 may be precisely calibrated so that channel 42 will only contain a predetermined quantity of fluid. Once the volume of channel 42 has been calibrated, channel 42 will consistently and reproducibly contain and dispense this liquid volume, provided that the channel is fully filled and preferably filled to overflowing. For example, FIGS. 3, 4 and 4A illustrate a pipette tip 30 having a channel 42 which has a calibrated volume equal to 15 $\mu$L of fluid. As will be described in greater detail below, if pipetter assembly 10 intentionally or unintentionally draws more than 15 $\mu$L of fluid, the inner end of wall 40 defining overflow opening 46 will shed or discard the fluid in excess of 15 $\mu$L from channel 42 so that only 15 $\mu$L of fluid occupies channel 42. Since excess fluid 53 (FIG. 4A) is shed into reservoir portion or volume 50 of the tip, and since reservoir volume 50 is positioned so as to be out of communication (below) with overflow opening 46, it will be seen that only 15 $\mu$L of fluid can be dispensed from pipette tip 30 when a positive pressure is created by the pipetter.

The volume of channel means 42 typically ranges between 1 $\mu$L to 500 $\mu$L, although even larger calibrated volumes can be provided. The volume of channel 42 is controlled by selecting core pins of various sizes, which, in combination with the mold, define tubular wall portions 38 and 40. FIGS. 6 and 7 illustrate an alternative embodiment of the present invention in which channel means 42 has been calibrated to contain a larger volume of fluid, for example, 75 $\mu$L of fluid. By varying the length and cross-sectional area of channel 42, the calibration volume may be increased or decreased. It is advantageous, however, to have channel bore 42 formed as a capillary tube. For injection-molded plastics, bore 42 should have a minimum taper or no taper at all, while still permitting release of the core pin.

The pipette tip of the present invention provides, therefore, an apparatus for accurately and consistently dispensing a calibrated volume of fluid. Moreover and very importantly, dispensing calibrated volumes is substantially independent of inaccuracies of pipetter 10 and/or inaccuracies in the user's technique. Thus, variations resulting from pipetter inaccuracy and technician error generally will not greatly reduce the accuracy of the fluid volume dispensed from channel 42 during pipetting. Further, the environmental factors are not as likely to affect the present pipette tip's performance, as compared to the adverse influence which such factors can have on pipetters. For example, the ambient heat or a technician's warm hands, which can cause significant thermal expansion of the piston/cylinder arrangement in a pipetter, will generally not affect the dispension accuracy of channel 42. This is because the pipette tip is sufficiently isolated from pipetter assembly 10, is not touched by the technician, and may be formed of low thermal expansion materials. Moreover, the improved pipette tip of the present invention eliminates the need to precisely calibrate adjustable pipetters. The pipetter need only be adjusted to the desired volume or to slightly overdraw channel 42. Thus, the accuracy of pipetting is no longer as dependant on the accuracy and precision of calibration of the pipetter. The present invention, accordingly, is not only more accurate, but also more efficient by reason of saving recalibration time, since each tip can be formed from a mold producing a calibrated volume, namely, tip calibration occurs during manufacture.

In order to cause excess fluid to be automatically and reproducibly shed or sloughed-off of overflow opening 46, an inclined surface 58 is preferably provided on the inner end of tube wall 40, which defines overflow opening 46. Accordingly, surface 58 is angularly inclined to a horizontal plane 35 at an angle of inclination $\theta$, as shown in FIG. 4.

When fluid 54 is drawn into channel 42 in an amount in excess of its capacity, the surface tension forms a fluid droplet 56 (FIG. 4) at overflow opening 46. In accordance with the present invention, overflow opening 46 is dimensioned and surface 58 sloped such that when an excess fluid droplet 56 forms at opening 46, the weight of the droplet is sufficient to overcome the surface tension. Accordingly, droplet 56 shears off from fluid 54 retained in channel 42. Fluid droplet 56 drops down into reservoir portion 50 in interior volume 34 of the pipette tip, as shown in FIG. 4A, where excess shed fluid 53 collects and puddles.

For instance, if channel 42 is calibrated for 15 $\mu$L, and 17 $\mu$L is drawn through channel 42, then 2 $\mu$L will be shed by overflow opening 46 into tip reservoir or lowermost portion 50. Subsequently, 15 $\mu$L may be accurately dispensed from pipette tip 30 while the 2 $\mu$L excess fluid is trapped and retained in portion 50. The excess liquid 53 is sufficiently below overflow opening 46 that it cannot flow back into channel 42 when the tip is pressurized to dispense liquid 54 remaining in channel 42.

The angle of inclination $\theta$ of surface 58 must be sufficiently inclined so that fluid characteristics, such as density, surface tension and viscosity, produce gravity shedding or sloughing when the pipette tip is in a near-vertical orientation. If $\theta$ is equal to zero or a relatively small angle, as shown in FIG. 7B, then the size of droplet 56 can vary by an amount causing precision to begin to become a function of pipetting technique. Accordingly, in the preferred form, and for most liquids of the type employed in high-volume pipetting, $\theta$ should be relatively steep, for example, downwardly inclined from a horizontal plane by between about 70 degrees to about 80 degrees. Lesser angles are suitable, if, for example, less precision is required or larger volumes are dispensed.

While not preferred, inner end 40 of the channel means can terminate in a flat or horizontal surface 58' (FIG. 7B) through which overflow opening 46 extends. When so constructed and $\theta$ is equal to zero or a low angle, a droplet shed-assisting technique, such as tapping or jarring the pipette tip in a direction transverse to axis 35 will knock or displace any excess droplet supported on surface 58'.

It also is preferable that overflow opening 46 have a relatively small diameter to assure precision in the volume of fluid remaining in channel 42. After shedding of excess liquid droplet 56, the surface tension in remaining liquid 54 causes a meniscus to form across overflow opening 46. Accordingly, a channel 42 having a relatively small diameter minimizes volume changes resulting from meniscus formation at overflow opening 46.

In order to prevent fluid from remaining on the inner end of the channel, it also is important that interior surfaces 52 of body 32 are at an annularly spaced distance which is sufficiently far away from overflow opening 46 and tube wall 40 so that droplets 56 cannot span, bridge or become supported between surface 52 and tube 40. Such spanning would interfere with the gravity-shedding process, and could cause excess fluid droplet 56 to remain atop opening 46, which would result in dispensing of droplet 56 and an inaccurate fluid delivery.

In the alternative embodiment of FIGS. 6 and 7, calibrating opening 46 extends through two downwardly inclined, oppositely facing planar surfaces 60 and 60', which intersect at about centerline 35 of the inner end of tube 40. Accordingly, as excess fluid flows out opening 46, it is gravity-shed off of both sides of tube 40 in order to maintain a precise, calibrated volume of fluid in channel 42. Again, the physical characteristics of the fluid and tube end defining opening 46 enable a reproducible volume of fluid to predictably remain in channel 42.

FIG. 7A illustrates a further alternative configuration of the protruding inner end 40 of channel 42. A conical surface 60 slopes away from the center line so as to produce gravity-shedding of liquid, but end 65 at the opening is substantially normal to longitudinal channel axis 35, making volume calibration somewhat easier to accomplish.

FIG. 7C illustrates a protruding inner end 40 of channel means 42 in which overflow opening 46 is positioned in a side wall 65 of the inner end. Thus, channel section 42a extends transversely to the inner end and longitudinal axis 35 at overflow opening 46 so as to cause overflow fluid being drawn into reservoir 50 be discharged in a direction toward a side wall of hollow tip body 32. This side-discharge structure acts as a protective baffle or barrier which reduces the chance of having overdrawn fluid squirt, or sprayed, up into the pipetter if, for example, the pipetter should be set for an overdraw and released too rapidly. The location of overflow opening 46 in side wall 65 of protruding inner end 40 of channel means 42 also can be employed as a structure to produce preferential overflow of fluid relative to partitions provided in the pipette tip reservoir 50, as described in more detail below.

Referring back to FIGS. 3 and 4, hollow body 32, of pipette tip 30, includes a pipette mounting end 36 proximate its upper portion. Pipette mounting end 36 is dimensioned to be releasably frictionally retained on tip-mounting end 24 of pipetter 10. Accordingly, the interior perimeter wall of body 32 preferably tapers inwardly as it extends downward from the upper perimeter lip 68. This taper substantially conforms to the taper of the exterior surface of tip mounting end 24 so that, upon sliding engagement therebetween, a seal can be formed which will allow pressure differences to be created and maintained inside tip 30.

In order to use pipette tip 30 of the present invention, therefore, tip 30 is slid onto the exterior surface of tip-mounting end 24 until lip 68 abuts the pipetter base portion 25. After adjusting pipetter 10 to slightly overdraw the volume capacity of channel 42, button 14 may be depressed which displace the volume of air within the cylinder. Subsequently, fluid intake end 38 is inserted into the fluid to be pipetted. Button 14 may be released, drawing fluid 54 into channel 42 through intake opening 44. All fluid drawn in excess of the volume of channel 42 is shed into reservoir portion 50, by the configuration of the inner end of tube 40 at overflow opening 46. Thus, channel 42 retains a precise calibrated volume of the fluid, which then may be dispensed or discharged from channel 42 through opening 44 by again depressing button 14 on pipetter 10.

Tip 30 can be injection-molded from various relatively chemically-unreactive plastics at low cost, making the pipette tip disposable. One of the advantages of injection-molding is that pulling the core pin from the still-warm plastic smooths the surface of channel or bore 42. This increases the reproducibility of the calibrated channel and minimizes the calibrated volume variation from sample to sample. Tip 30 also can be formed from glass, ceramics or the like. Moreover, tip 30 can be integrally formed with the negative pressure generating device or "pipetter". Thus, the tip can be provided in one end of a pipetter and a resiliently flexible bulb releasably attached to the other end. The bulb would be removed to drain overflow liquid from the combined pipetter/tip device. Furthermore, tip apparatus 30 of the present invention will perform equally well with either a "to-deliver" pipetter or a "to-contain" pipetter, as long as an overdraw and over-delivering of calibrated channel 42 can be accomplished.

From the above description of the pipette tip of the present invention, it will be seen that the tip affords a new and highly useful method of dispensing a calibrated volume of a fluid, and particularly a liquid. The method of the present invention, therefore, includes the steps of urging a fluid into fluid channel 42 in a hollow pipette tip 30. Channel 42 has a calibrated volume and an overflow opening 46. The urging step is continued until the fluid fills channel 42 and overflows out of the overflow opening 46. Thereafter, the present method includes the step of displacing fluid 54 remaining in channel 42 from the channel to dispense a calibrated volume of liquid.

The urging step preferably is accomplished by creating a negative pressure inside tip 30 to draw the fluid up into channel 42, but it also would be possible to apply a positive pressure to the fluid outside the tip to urge or force the fluid up into channel means 42 until overflowing occurs. Similarly, displacing remaining fluid 54 is preferably accomplished by creating a positive pressure inside tip 30, but for some tips merely opening the tip to atmospheric pressure or applying a negative outside pressure could be used.

The method of the present invention preferably includes the further steps of mounting the tip on a pipetter and gravity-shedding excess fluid from overflow opening 46, usually when the calibrated channel is in a near-vertical orientation.

One important advantage of the pipette tip of the present invention is that it enables accurate liquid volumes to be dispensed using a very inexpensive pipetter. Typically, an adjustable volume pipetter which is capable of reproducible and reasonably accurate dispensing of liquid volumes will cost about $150 to $200. Fixed volume pipetters, which generally are less accurate and are not adjustable, cost $20 or less. Using the calibrated pipette tip of the present invention, fixed pipetters capable of an overdraw of, for example, 10 to 20 percent of calibrated channel 42, may be used to reproducibly dispense accurate liquid volumes.

The cost of a pipette tip which is not calibrated is about 2 to 3 cents and a calibrated tip will cost about 4 to 5 cents. Thus, a very substantial savings can be realized by using calibrated pipette tips 30 in combination with a pipetter 10 having a fixed volume at least equal to the volume of calibrated channel means 42.

The pipette tip of the present invention has the additional advantage of being constructed in a manner which enables it to be used as a container to capture fluid overflowing from the overflow opening. The position of overflow opening 46 well above the bottom of the interior volume 34 of the body so as to define a reservoir portion 50 provides a structure which will hold fluid materials, and particularly liquids, in a stable or non-flowing condition. Liquids placed in reservoir 50 will be contained therein as long as the pipette tip is in a generally vertical orientation.

As can be seen in FIG. 6, for example, the volume of reservoir 50 below overflow opening 46 can be substantial. This reservoir volume is not found in conventional pipette tips in that liquids or other substances in the tip can gravitate and/or be urged by the pipetter out the intake channel. The pipette tip of the present invention, therefore, also can be used as a container for applications, such as, storing fluid which overflows into reservoir 50 and/or reacting the liquid with a reagent or other substance placed in the reservoir.

Either liquid or solid reagents may be positioned in reservoir 50, preferably in advance of drawing liquid. The fluid to be pipetted and reacted with the reagent in reservoir 50 is then drawn into channel 42 until it overflows into the reservoir. When a chemically effective amount of liquid has been over-drawn into the reservoir, the combined liquid and reagent can be stored or allowed to react in reservoir volume 50 of pipette tip 30.

Using the pipette tip of the present invention, therefore, it is possible to perform various testing and diagnostic procedures inside the pipette tip. Polymerase chain reaction (PCR) testing in the biochemical field and pH testing in the chemical field are among the many applications to which the present pipette tip is well-suited. Virtually any test in which a change of color occurs to indicate the test result is a candidate for a partitioned pipette tip.

When used as a reaction or storage vessel, tip 30 may not be required to dispense a precise volume to internal reservoir 50. Nevertheless, a relatively precise volume can be drawn into internal reservoir 50 by setting pipetter 10 to overdraw the calibrated channel volume by a desired calibrated amount to be pulled into interior reservoir 50. Moreover, an approximate volume can be achieved by filling channel 42 until a droplet starts to appear at overflow opening 46. The intake opening 44 then may be taken out of the source liquid. The pipetter can be used to draw air into intake opening 44 until channel 42 is emptied into the interior of the pipette tip, namely, into internal reservoir portion 50.

In order to provide even more flexibility in using the pipette tip of the present invention as a reaction container or vessel, it is a further feature of the present invention to form the pipette tip with an interior partition. In FIGS. 8 and 9, therefore, pipette tip 30a is formed with a body 32a defining an interior volume 34a. Mounted to extend through end wall 71 of body 32a is a tube 40a defining channel means 42a. Channel means 42a extends from intake opening 44a to an overflow opening 46a positioned to define a reservoir volume 50a below the overflow opening capable of storing liquids in a stable condition.

Since reservoir volume 50a is closed by end wall 71 and is below opening 46, substances, such as diagnostic reagents, also can be contained in a stable condition in the reservoir. As shown in FIGS. 8 and 9, therefore, reservoir 50a is subdivided by partition means 72 so as to define a plurality of sub-volumes or reservoirs 73 and 74. By way of an example, a liquid 76 is shown positioned in sub-volume 73 and a solid substance 77 is shown positioned in sub-volume 74.

As can be seen in the drawing, surface 58a will bias or cause preferential overflow of pipetted liquid 56a into a preferred reservoir, in this case 74, sub-volume for contact with substance 77. The reaction between substance 77 and liquid 56a can then be observed. Thereafter, the technician can tilt the pipette tip until liquid 76 can flow into sub-volume 74 over partition 72. Liquid substance 76 can be a further reagent, a neutralizing compound, or a dye or marking liquid, to name only a few possibilities.

In pipette tip 30b of FIGS. 10 and 11, the inner end of tube 40b is formed with an inwardly tapered conical surface 58b which defines overflow opening 46b. Transversely extending partition 81 divides reservoir volume 50b into two sub-volumes 82 and 83. The substantially horizontal rim 84 of tube 40b and the position of partition 81 in a plane bisecting opening 46b will result in flow of overflow liquid approximately equally into sub-volumes 82 and 83. Alternatively, pipette tip 30b can be tipped to one side, and then the other, during drawing liquid to ensure overflow of liquid into both sub-volumes 82 and 83.

A pipette tip constructed in the manner of tip 30b can, therefore, be used for comparison of the reactions between liquid 56b and various substances placed in the sub-volumes. Alternatively, a reagent may be placed in one side and small volumes of liquid drawn into both sub-volumes in a titration process in which the volume threshold producing a color change, as compared to the original liquid color, is sought to be observed.

If the pipette tip further has a calibrated channel, 42a, 42b, it also can be used for precise dispensing of liquids. A calibrated intake channel means, however, is not required in the broadest form of this aspect of the present invention.

In order to enable transportation and/or storing of partitioned pipette tips, an optional enclosure means or cap assembly 86 may be provided. Cap 86 is dimensioned for sliding receipt on end 36b of the tip body once the tip has been removed from the pipetter. In the preferred form, a downwardly depending pin or plug 87, having a conical end 88, engages mating conical surface 58b in inner end 40b of the tip intake channel. Cap 86, therefore, not only closes open pipetter mounting end 36b, but also closes overflow opening 46b and channel 42b.

Pipette tip 30b and cap assembly 86, therefore, can be used for chemical procedures that require considerable time to complete. Once the liquid is drawn, the tip can be removed from the pipetter, capped and placed in a rack while the reaction takes place. Similarly, capped pipette tip 30b can be shipped or transported, stored for extended periods, and the contents of the tip even may be freeze-dried while in the tip. Capping of tip 30b also allows shaking or agitation of the tip to mix its contents, and reduces the likelihood of contamination of the contents.

It will be appreciated that various mating or interengaging cap structures can be provided to close overflow opening 46b and end opening 36b.

In another aspect, therefore, the method of the present invention includes the step of urging fluid into the intake channel of a pipette tip having an interior volume until it overflows into a reservoir portion and is contained in the pipette tip in a stable condition, i.e., the liquid is not moving or flowing out of the reservoir portion. Additionally, the present method includes the steps of storing the liquid in the reservoir portion and/or contacting the liquid while in the reservoir with a substance, such as, a diagnostic reagent. Finally, the present method also may include the step of partitioning the liquid overflowing into the reservoir into a sub-volume in the reservoir to enable use of the pipette tip as a container or vessel for carrying out chemical and/or biochemical procedures and/or storing or transporting the specimen.

What is claimed is:

1. A pipette tip comprising:
    a hollow body defining an interior volume, said body having channel means with a longitudinal axis, said channel means extending from a fluid intake opening to a fluid overflow opening and having surface means defining said overflow opening inclined relative to said longitudinal axis by an amount sufficient to produce gravity shedding of fluid overflowing from said opening when said longitudinal axis is in a substantially vertical orientation,
    said overflow opening being positioned for overflow of fluid from said channel means into said interior volume, and
    said channel means having a calibrated volume between said intake opening and said overflow opening.

2. The pipette tip as defined in claim 1 wherein,
    said body defines a reservoir portion of said interior volume positioned below said overflow opening, and
    said channel means has an inner end and a channel section at said inner end extending transversely to said inner end and terminating in said overflow opening positioned in a side wall of said inner end at a location sufficiently above said reservoir volume for gravity shedding of fluid into said reservoir portion.

3. The pipette tip as defined in claim 1, further comprising:
    mounting means for providing an opening being positioned proximate to an end of said body opposite said channel means, and
    said overflow opening being positioned to extend through said surface means.

4. The pipette tip as defined in claim 3 wherein,
    said surface means is downwardly inclined when said longitudinal axis is vertically oriented at an angle of between about 70 degrees to about 80 degrees relative to a horizontal plane.

5. The pipette tip as defined in claim 3 wherein,
    said surface means is provided by two downwardly inclined, oppositely facing surfaces.

6. The pipette tip as defined in claim 5 wherein,
    said inclined oppositely facing surfaces each are downwardly inclined when said longitudinal axis is vertically oriented at an angle of between about 70 degrees to about 80 degrees relative to a horizontal plane.

7. The pipette tip as defined in claim 3 wherein,
    said surface means is provided by a downwardly and outwardly tapering conical surface.

8. The pipette tip as defined in claim 1 wherein,
    said pipette tip is formed form an injection-molded plastic material as an integrally formed member.

9. The pipette tip as defined in claim 1 wherein,
    said interior volume is defined by an interior surface of said body; and
    said channel means protrudes into said interior volume and is sufficiently annularly spaced from said interior surface to permit fluid overflowing from said overflow opening to move in a direction away from said overflow opening and into said interior volume.

10. The pipette tip as defined in claim 1 wherein,
    said body defines a reservoir portion below said overflow opening suitable for containment of said fluid in a stable condition, and
    said reservoir portion has a sufficiently large volume to contain a substance to be contacted by said fluid and a chemically effective volume of said fluid.

11. The pipette tip as defined in claim 1 wherein,
    said body defining said interior volume includes a wall dividing said interior volume into a plurality of sub-volumes.

12. The pipette tip as defined in claim 11 wherein,
    said overflow opening is formed and positioned for overflow of fluid into a selected one of said sub-volumes.

13. The pipette tip as defined in claim 1, and pipetter mounted to said pipette tip by mounting means, said pipetter being formed to draw a volume of said fluid known to be in excess of said calibrated volume of said channel means.

14. A pipette assembly comprising:
    a pipette tip having a hollow body defining an interior volume, said body being formed with channel means extending from an intake opening to an overflow opening communicating with said interior volume, said overflow opening being positioned for overflow of a liquid taken into said channel means into a reservoir portion of said interior volume positioned below said overflow opening, said channel means having a predetermined calibrated volume between said intake opening and said overflow opening and said channel means is formed for gravity-sloughing of liquid from said overflow opening into said reservoir portion when said channel means is oriented in a substantially vertical orientation; and said body being further formed with a mounting opening for mounting said pipette tip to a pipetter device for urging said liquid into said interior volume through said channel means; and
    a pipetter device mounted to said pipette tip by said mounting opening, said pipetter device being formed to draw a volume of liquid into said channel means known to be in excess of said calibrated volume of said channel means.

15. A pipette tip comprising:
    a hollow body defining an interior volume, said body having channel means extending from a fluid intake opening to a fluid overflow opening positioned for overflow of fluid from said channel means into said interior volume, and
    wall means provided in said interior volume and dividing said interior volume into a plurality of sub-volumes.

16. The pipette tip as defined in claim 15 wherein,
    said overflow opening is positioned for the overflow of fluid into less than all of said sub-volumes.

17. The pipette tip as defined in claim 15 wherein,
    said overflow opening is positioned for the overflow of fluid into a plurality of said sub-volumes.

18. The pipette tip as defined in claim 15 wherein, said channel means has a calibrated volume between said intake opening and said overflow opening.

19. A method of dispensing a calibrated volume of fluid using a pipette comprising the steps of:

orienting a hollow pipette tip having a channel means with a calibrated volume in a substantially vertical orientation;

urging a fluid into said channel means until said fluid fills said channel means and overflows out of said channel means through an overflow opening;

gravity-shedding excess fluid overflowing from said overflow opening; and after said urging step, displacing the fluid remaining in said channel means from said channel means to dispense a calibrated volume of said fluid.

20. The method as defined in claim 19, and the additional step of:

during said urging step, containing fluid overflowing from said channel means in a reservoir portion of an interior volume in said hollow pipette tip; and contacting said fluid contained in said reservoir portion with a substance placed in said reservoir portion.

21. The method as defined in claim 20 wherein, prior to said urging step, placing a diagnostic reagent in said reservoir portion.

22. A method of dispensing a calibrated volume of fluid, comprising the steps of:

a) urging a fluid through an inlet orifice into an elongate, hollow receptacle having a calibrated volume and an overflow orifice;

b) orienting said elongated receptacle along a substantially vertical axis with said overflow orifice above said inlet orifice;

c) overflowing the fluid out of an overflow orifice of said receptacle after filling completely the calibrated volume of the receptacle;

d) removing fluid in excess of said calibrated volume from said overflow orifice solely by gravity-shedding said fluid from said overflow orifice during the overflowing step; and e) displacing the fluid remaining in the calibrated volume of the receptacle after the overflowing step, thereby dispensing a calibrated volume of fluid.

23. The method of claim 22 further including the steps of:

a) capturing the overflowing fluid in a second receptacle associated with the calibrated volume of the receptacle, said second receptacle being divided into a plurality of reservoirs; and b) biasing the overflowing liquid so as to flow into a preferred reservoir within the second receptacle.

24. A pipette tip comprising:

a hollow body defining an interior volume, said body having channel means extending from a fluid intake opening to a fluid overflow opening, said body and channel means being formed as an integrally formed member from a plastic material, said overflow opening being positioned for overflow of fluid from said channel means into said interior volume, and said channel means having a calibrated volume between said intake opening and said overflow opening and a gravity-shedding surface means surrounding said overflow opening for sloughing of fluid under the influence of gravity when said channel means is in a substantially vertical orientation.

* * * * *